(12) United States Patent
Meyers et al.

(10) Patent No.: US 9,345,618 B2
(45) Date of Patent: May 24, 2016

(54) OCULAR DEVICE

(71) Applicant: CRT Technology Inc., Mesa, AZ (US)

(72) Inventors: William E. Meyers, Scottsdale, AZ (US); Hermann H. Neidlinger, San Jose, CA (US)

(73) Assignee: CRT Technology Inc., Mesa, AZ (US)

( * ) Notice: Subject to any disclaimer, the term of this patent is extended or adjusted under 35 U.S.C. 154(b) by 2 days.

(21) Appl. No.: 14/225,786

(22) Filed: Mar. 26, 2014

(65) Prior Publication Data

US 2014/0296865 A1 Oct. 2, 2014

Related U.S. Application Data

(60) Provisional application No. 61/805,292, filed on Mar. 26, 2013.

(51) Int. Cl.
*G02C 7/04* (2006.01)
*A61F 9/00* (2006.01)

(52) U.S. Cl.
CPC ................ *A61F 9/0061* (2013.01); *G02C 7/04* (2013.01)

(58) Field of Classification Search
CPC .................. A61F 9/0061; G02C 7/04; A61M 2210/0612; A61M 5/46
USPC ........... 294/1.2; 604/294, 295, 297, 298, 301; 606/107, 108, 166; 351/159.02–159.38, 247
See application file for complete search history.

(56) References Cited

U.S. PATENT DOCUMENTS

| | | | | |
|---|---|---|---|---|
| 3,910,618 A * | 10/1975 | Massenz | | 294/1.2 |
| 4,113,297 A * | 9/1978 | Quinn | | 294/1.2 |
| 4,994,080 A * | 2/1991 | Shepard | | 623/6.64 |
| 6,200,291 B1 * | 3/2001 | Di Pietro | | A61M 5/46 604/117 |
| 6,312,403 B1 * | 11/2001 | Ruiz | | A61F 9/007 604/23 |
| 2004/0196430 A1 * | 10/2004 | Graham | | 351/178 |
| 2006/0235514 A1 * | 10/2006 | Silvestrini | | 623/5.13 |
| 2012/0265149 A1 * | 10/2012 | Lerner | | A61F 9/0017 604/190 |

* cited by examiner

*Primary Examiner* — David C Eastwood
*Assistant Examiner* — Mikail Mannan

(57) ABSTRACT

The present disclosure relates to a contact lens comprising a channel extending therethrough, an ocular device configured to engage with the channel, and related kits and methods that provide for improved contact lens insertion, cleaning and removal, as well as ocular safety and health.

14 Claims, 3 Drawing Sheets

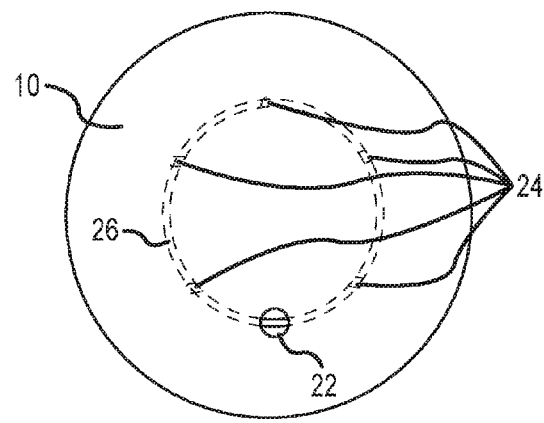
FIG.2D
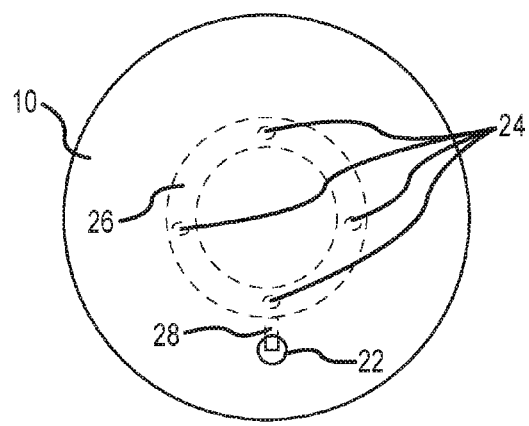
FIG.2E
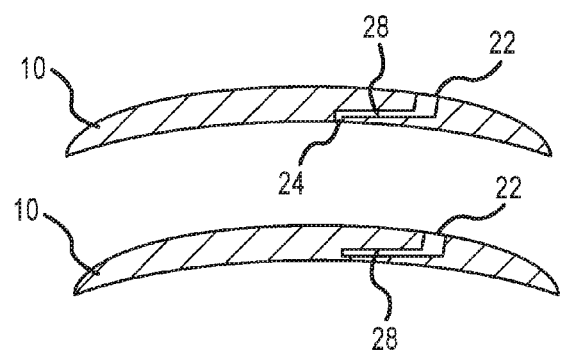
FIG.2F
FIG.2G

OCULAR DEVICE

CROSS-REFERENCE TO RELATED APPLICATIONS

This Non-Provisional Patent Application claims priority to and the benefit of U.S. Provisional Patent Application Ser. No. 61/805,292 entitled OCULAR DEVICE and filed Mar. 28, 2013, which is incorporated by reference herein in its entirety.

BACKGROUND

1. Field

The present disclosure relates generally devices, kits and methods that provide for improved contact lens insertion, cleaning and removal, as well as ocular safety and health.

2. Discussion of the Related Art

The most common method of inserting a contact lens onto an eye involves placing a contact lens, wetted with an appropriate fluid, on the fingertip, properly positioning the contact lens in front of the eye, and placing the contact lens on top of the eye while keeping the eyelids open.

This method is neither easy nor accurate, and can damage the cornea since the eye cannot focus on the lens or the finger as the finger is brought close to the eye. Thus, the final step of actually placing the lens on the cornea in the proper position is guesswork to a substantial degree.

In view of the difficulties with respect to the proper positioning and insertion of contact lenses, devices have been developed to assist in handling, inserting and removing a contact lens from the eye, such as suction cup devices. However, there often exist circumstances, that in certain extreme environments, contaminants could "bake" contact tenses onto the cornea, or get trapped under the contact lens, causing harm to the wearer if not removed in a timely manner. In such cases, the commonly available suction cup devices may have limited use or could harm the wearers eyes when applied. For example, it has been found in the past that suction cups are not useful in removing soft contact lenses because they tend to pull the lens away from the eye rather than releasing the surface tension between the lens and the lachrymal fluid of the eye. As a result, corneal cells may be damaged. It has also been found that, in many cases, the cornea is too sensitive to allow removal of the lens without increasing the possibility of causing injury, however slight, to the eye.

Therefore, there exists a need for a device that not only provides stable, accurate and reproducible positioning and insertion of the contact lens onto the eyes, but also allows for alternate means of removal of the contact lens, should a simple suction cup device fail, such as by applying a positive relative pressure below the contact lens that lifts the contact lens from the cornea. Further, in certain contaminating environments and situations, such as accumulation of cell debris, metabolic byproducts and bacteria, it may be desirable to clean or irrigate the posterior lens zone without removing the lens from the cornea. There is thus a need for a device that allows "in vivo" irrigation or decontamination of the posterior zone. Furthermore, it can be difficult to administer medication, such as eye drops or creams, onto one's own eye while wearing contact lenses. This is particular true for the elderly and for people who have shaky hands. Contamination of the medication should also be avoided by preventing the medication container from contacting the eye or the surrounding tissues. There is thus a need for a device that provides accurate and reproducible application of medication and other objects onto the eyes while wearing contact lenses.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

FIG. 2D is a top view of a contact lens of the present disclosure having a central conduit;

FIG. 2E is a top view of a contact lens of the present disclosure having central and branch conduits;

FIG. 2F is a cross-sectional side view of a contact lens of the present disclosure having a conduit;

FIG. 2G is another cross-sectional side view of the contact lens of FIG. 2F;

DETAILED DESCRIPTION OF THE ILLUSTRATED EMBODIMENTS

Figure 1A:
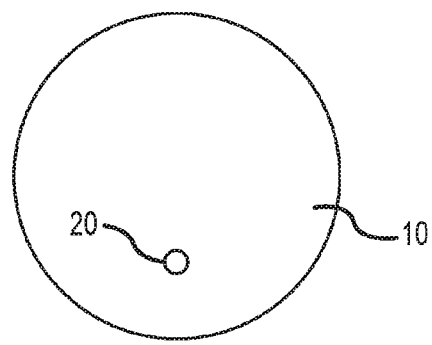
FIG. 1A is a top view of a contact lens of the present disclosure having one channel.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

Defects of the prior art are overcome in accordance with the present disclosure by a contact lens comprising at least one channel extending therethrough. An ocular device can be removeably coupled to the anterior surface of the contact lens about the channel, for example at a discrete location or annularly about the channel. As used herein, "anterior surface" refers to the surface meant to contact the eyelid while "posterior surface" refers to the surface meant to contact the eye. In addition, positive and/or negative relative pressure can be controllably applied, or a medication, irrigant, or solvent can be delivered, to name just a few, from the ocular device through the channel to the area between the cornea and the posterior surface of the contact lens. In this manner, devices, kits and methods are disclosed herein that provide for improved contact lens insertion, cleaning and removal, as well as ocular safety and health.

With reference to FIGS. 1A and 1B and 2A and 2B, embodiments of the present disclosure comprise a contact lens 10. Contact lens 10 can be a hard, semi-hard or soft lens, whether configured for vision correction, orthokeratology, aesthetics or display technology, to name just a few. Contact lens 10 can have an outer diameter of from about 5 mm to about 20 mm, with smaller or larger diameters being possible in special cases. By way of non-limiting example, a scleral contact lens can have an outer diameter of up to about 28 mm or more.

Contact lens 10 can be comprised of one or more of fluorosilicon acrylate, silicon acrylate, polymethylmethacrylate, a silicon hydrogel, or another suitable material. In general, any gas permeable or non gas permeable, biocompatible material is suitable for use herein.

In accordance with embodiments of the present disclosure, contact lens 10 comprises at least one channel 20, for example, up to six channels 20 or more, more preferably, one or two channels 20. As used herein, the term "channel" refers to a void extending partially or completely between the posterior surface and the anterior surface of contact lens 10.

The cross-section of a channel 20 can be of any shape, such as but not limited to, elliptical or non-elliptical. In this regard, as used herein, an "elliptical" shape refers to any shape that generally lacks a point where two lines, curves, or surfaces converge to form an angle. For example, an "elliptical" shape encompasses traditional Euclidian geometric shapes such as circles and ellipses, as well as other non-angular shapes (that lack any angles), even if those shapes do not have designations common in Euclidian geometry.

As used herein, a "non-elliptical" shape refers to any shape that includes at least one point where two lines, curves, or surfaces converge to form an angle. For example, a "non-elliptical" shape encompasses traditional Euclidian geometric shapes such as triangles, rectangles, squares, hexagons, trapezoids, and the like as well as other shapes that have at least one angle even if those shapes do not have designations common in Euclidian geometry. For example, a channel 20 may be slotted to control the rotational orientation of an ocular device configured to engage therewith. Such a slot may be linear or helical, for example to rotate an ocular device configured to engage therewith.

Figure 1B:
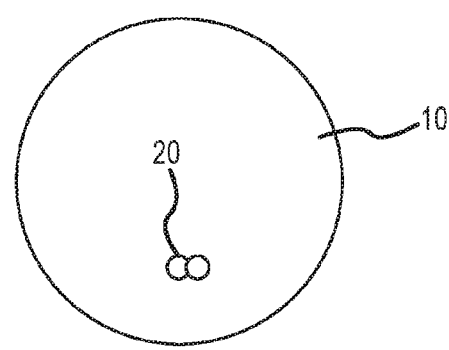
FIG. 1B is a top view of a contact lens of the present disclosure having offset channels.
Figure 2A:
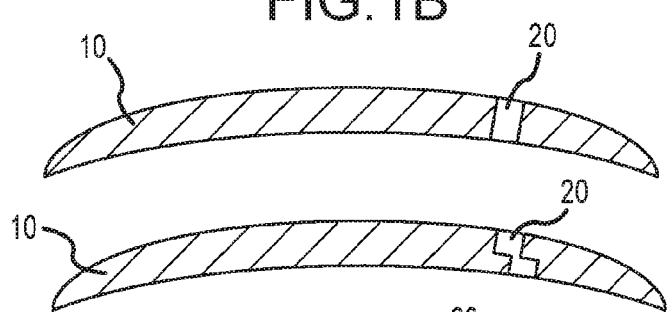
FIG. 2A is a cross-sectional side view of the contact lens of FIG. 1A.
Figure 2B:
FIG. 2B is a cross-sectional side view of the contact lens of FIG. 1B.
Figure 2C:
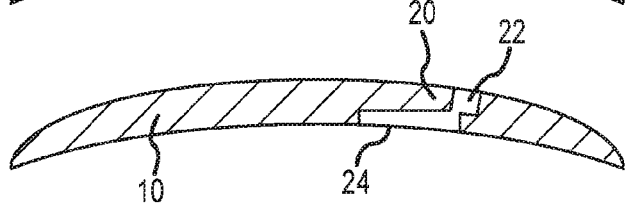
FIG. 2C is a cross-sectional side view of a contact lens of the present disclosure having offset channels.

The cross-section of a channel 20 can remain constant (e.g., cylindrical, for example as illustrated in FIGS. 1A and 2A) or vary (e.g., frustoconical, hourglass, tapered, offset) between the posterior surface and the anterior surface of contact lens 10, thereby adjusting the pressure and/or the delivery rate between the posterior and anterior surfaces in a predictable manner (e.g., according to Poiseuille's law). As alluded to, one or a plurality of channel 20 can be offset, for example as illustrated in FIGS. 1B, 2B and 2C. As used herein, "offset" refers to relative cross-sectional displacement or overlap of one or a plurality of channel 20, while still maintaining a pathway therethrough, for example through which positive and/or negative relative pressure can be controllably applied, or a medication, irrigant, or solvent can be delivered.

As used herein, a "channel" thus comprises one or a plurality of openings, referred to herein separately as an "opening" or more generally as a "channel." In regard to FIG. 2C, an anterior opening 22 on the anterior surface of contact lens 10 can be smaller than a posterior opening 24 on the posterior surface of contact lens 10. The embodiment illustrated in FIG. 2C may be especially useful where posterior opening 24 comprises an open zone and is configured to vault (i.e., not touch) the cornea.

Embodiments can comprise one or a plurality of channel 20, where there is not a one to one correspondence between the number of anterior openings 22 and the number of posterior openings 24. Indeed, there can be more or less of either on either side of contact lens 10. For example, and with reference to FIG. 2D, contact lens 10 can comprise a single anterior opening 22 and a plurality of posterior openings 24, the openings all in communication via a central conduit 26 within contact lens 10. Central conduit 26 may be spatially configured (e.g., in length, volume, pathway, etc.) to adjust (e.g., evenly or unevenly distribute) the pressure and/or the delivery rate between the openings in a predictable manner. Conduit 26 can comprise a complete toroidal shape, or less than a complete toroidal shape (e.g., 45, 90, 180, 270 degrees of a toroidal shape).

With reference now to FIG. 2E, contact lens 10 can comprise a branch conduit 28, in addition to or in lieu of a central conduit 26, to further adjust the positive and/or negative relative pressure and/or the delivery rate of a medication, irrigant, or solvent between a single anterior opening 22 and a plurality of posterior openings 24.

Yet another embodiment is illustrated in FIGS. 2F and 2G, the latter being another cross-sectional side view of the contact lens of FIG. 2F. In the depicted embodiment, an anterior opening 22 of contact lens 10 is larger than a posterior opening 24, the openings all in communication via a conduit 28.

So as to not compromise visual acuity, a channel 20, or a plurality of channels 20 as the case may be, and/or their respective openings, can be located away from the optic zone of contact lens 10, for example between the mid to outer periphery of contact lens 10. More specifically, a channel 20 can be located from about 3 mm to about 7 mm from the center of contact lens 10, more preferably from about 4 mm to about 5 mm from the center of contact lens 10.

In various embodiments, a circular channel 20, and/or its respective openings, can have a diameter of from about 0.1 mm to about 4 mm, more preferably from about 1 mm to about 2 mm. In other embodiments, a circular channel 20 can have a diameter of greater than about 1 mm, more preferably greater than about 2 mm or 3 mm. In general, the size of a channel 20 is sufficient to allow the application of pressure, or the delivery of a medication, irrigant, or solvent to the area between the cornea and the posterior surface of the contact lens, and not become blocked by fear fluid.

A channel 20 can be produced by lathe-cutting, drilling, molding and/or irradiation techniques, whether through contact lens 10 or a blank or button from which contact lens 10 is to be manufactured. A channel 20 can thus be produced during the manufacture of contact lens 10. In other embodiments, a channel 20 can be produced while contact lens 10 is on a patient, for example in connection with a depth control mechanism as described infra so as to not damage the patient's cornea.

Figure 3:
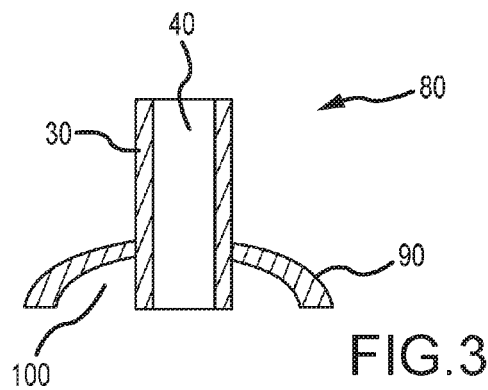
FIG. 3 is a cross-sectional side view of an embodiment of an ocular device.

With reference now to FIG. 3, an ocular device 80 can be removeably coupled to the anterior surface of contact lens 10 about a channel 20, for example at a discrete location or annularly about a channel 20. Ocular device 80, in various embodiments of the present disclosure, comprises a hollow tubing 30 having an inner diameter 40, and a cup member 90. Hollow tubing 30 generally extends through cup member 90, whether though the center thereof as illustrated or off-center, and whether orthogonal thereto as illustrated or at an angle, thereby creating an annular space 100. In various embodiments, cup member 90 is hemispherical. In various embodiments, a distal edge of hollow tubing 30 and a distal edge of cup member 90 are coplanar.

Cup member 90 and hollow tubing 30 can each be made of different or the same flexible, pliable, biocompatible material, such as a plastic or rubber, polyolefins or other suitable thermoplastic elastomers.

In various embodiments of the present disclosure, at least one of cup member 90 and hollow tubing 30 is made of a material which holds its shape yet which can be distorted while its distal edge is in contact with the surface of contact lens 10 to produce and temporarily maintain negative relative pressure within annular space 100, as with an annular suction cup. In this manner, ocular device 80 can be removeably coupled to the anterior surface of contact lens 10 about a channel 20. To facilitate removal of ocular device 80 from contact lens 10, cup member 90 can comprise a tab or weakened portion which, when pulled or otherwise actuated, breaks a seal between ocular device 80 and contact lens 10.

In various embodiments of the present disclosure, the edges of cup member 90 and hollow tubing 30 can be rounded in profile and generally free from configuration irregularities that may be injurious to the cornea (e.g., seams or mold marks). In various embodiments, the diameter of cup member 90 is slightly less than one-half the diameter of contact lens 10.

Figure 4:
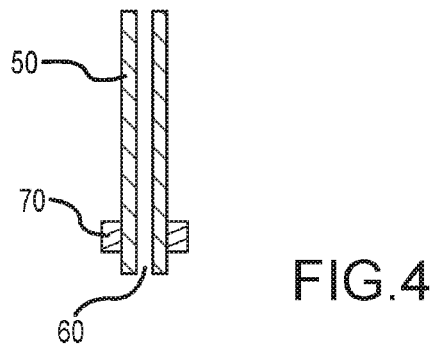
FIG. 4 is a cross-sectional side view of an embodiment of a second hollow tubing.

In various embodiments of the present disclosure, and with reference now to FIG. 4, ocular device 80 can further comprise an elongate element 50 having an outer diameter 60, which is smaller than inner diameter 40 of hollow tubing 30. In various embodiments, an end of elongate element 50 can be configured to engage with a channel 20. The docking of an end of elongate element 50 with a channel 20 can be facilitated by integrated "sensing" elements, such as magnetic or electromagnetic elements. Elongate element 50 can be axially slideable and removeable with respect to hollow tubing 30.

In various embodiments, elongate element 50 is solid, while in other embodiments, elongate element 50 is hollow. Embodiments wherein elongate element 50 is solid may be useful in connection with producing a channel 20 while contact lens 10 is on a patient.

Figure 5:
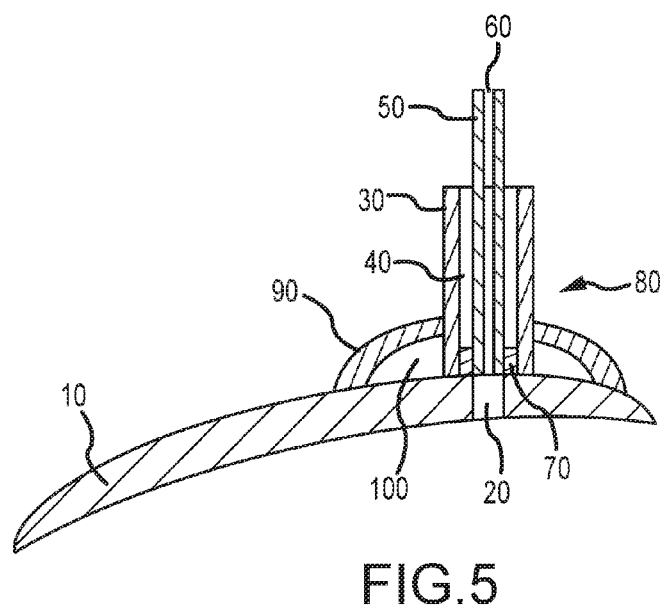
FIG. 5 is a cross-sectional side view of an embodiment of an ocular device having a second hollow tubing.

In embodiments wherein elongate element 50 is hollow, and with reference now to FIG. 5, positive and/or negative relative pressure can be controllably applied (e.g., by a pressure bulb, mouth piece or vacuum), or a medication, irrigant, or solvent can be delivered, to name just a few, from ocular device 80 through a channel 20 to the area between the cornea and the posterior surface of contact lens 10.

Elongate element 50 can further comprise a depth control mechanism, for example, a stop 70 near an end of elongate element 50 as illustrated in FIGS. 4 and 5, to prevent elongate element 50 from penetrating completely through a channel 20 toward the corneal surface. Alternate depth control mechanisms can comprise incorporating more than one channel 20 which are offset, for example as illustrated in FIGS. 1B and 2B, incorporating one or more slots into a channel 20 which correspond to one or more protrusions on an end of elongate element 60, varying the cross-section of a channel 20 between the posterior surface and the anterior surface of contact lens 10, to name just a few.

Embodiments of the present disclosure further comprise kits having at least one contact lens with at least one channel extending therethrough, as described supra. For example, a kit may contain at least one pair of contact lenses (e.g., sufficient to be worn by a patient for a day, week, month, year, etc.). Other embodiments of the present disclosure comprise kits having at least one contact lens and at least one ocular device configured to engage with a channel, both as described supra.

Methods of use herein can comprise removeably coupling an ocular device as described supra to an anterior surface of a contact lens, performing one or more additional ocular procedures described infra, and de-coupling the ocular device from the anterior surface of the contact lens.

Coupling can be accomplished by distorting the shape of at least one of a cup member and a hollow tubing while its distal edge is in contact with the surface of a contact lens to produce and temporarily maintain negative relative pressure within an annular space. A temporary (e.g., bioabsorbable) adhesive may also be used. De-coupling can be accomplished by breaking a seal between the ocular device and the contact lens, for example by pulling or otherwise actuating a portion of the ocular device or a tab or weakened portion.

One additional ocular procedure may further comprise using the ocular device to insert a contact lens onto the eye of a patient. Another additional ocular procedure may further comprise using the ocular device to clean a contact lens while on the eye of a patient, comprising a step of delivering an irrigant or solvent to the area between the cornea and the posterior surface of the contact lens irrigants and solvents suitable for use include but are not limited to water, saline and the like.

Yet another additional ocular procedure may further comprise using the ocular device to remove a contact lens from the eye of a patient, comprising a step of applying positive and/or negative relative pressure to the area between the cornea and the posterior surface of the contact lens. Still another additional ocular procedure may further comprise using the ocular device to remove a contact lens from the eye of a patient, comprising a step of delivering an irrigant or solvent to the area between the cornea and the posterior surface of the contact lens.

Another additional ocular procedure may further comprise using the ocular device to deliver a medication to the area between the cornea and the posterior surface of a contact lens. Medications suitable for use include but are not limited to eye drops, creams, steroids, antihistamines, sympathomimetics, beta-receptor blockers, parasympathomimetics, parasympatholytics, prostaglandins, non-steroidal anti-inflammatory drugs (NSAIDs), topical anesthetics and the like.

It will be apparent to those skilled in the art that various modifications and variations can be made in the present disclosure without departing from the spirit or scope of the disclosure. For example, while the present disclosure is described primarily with reference to contact lenses, the present disclosure can be applied to various other medical and non-medical devices. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. An ocular device comprising:
a hollow tubing extending through a cup member to create an annular space within which a negative relative pressure can be produced and temporarily maintained while the ocular device is in contact with an anterior surface of a contact lens;
an elongate element having an outer diameter, which is smaller than an inner diameter of the hollow tubing, wherein the elongate element is axially slideable and removeable with respect to the hollow tubing, wherein the elongate element comprises a depth control protrusion and the contact lens comprises a depth control slot for controlling the depth of the elongate element.

2. The ocular device of claim 1, wherein the cup member is hemispherical.

3. The ocular device of claim 1, wherein a distal edge of the hollow tubing and a distal edge of the cup member are coplanar.

4. The ocular device of claim 1, wherein the negative relative pressure can be produced and temporarily maintained within the annular space while a distal edge of the cup member is in contact with the anterior surface.

5. The ocular device of claim 1, wherein the elongate element is hollow.

6. The ocular device of claim 5, wherein positive and/or negative relative pressure can be controllably applied through a channel extending between a posterior surface of the contact lens and the anterior surface to an area between a patient's cornea and the posterior surface.

7. The ocular device of claim 5, wherein a medication, irrigant, or solvent can be delivered through a channel extending between a posterior surface of the contact lens and the anterior surface to an area between a patient's cornea and the posterior surface.

8. The ocular device of claim 6, wherein the channel has a diameter from about 0.1 mm to about 4 mm, and wherein the channel is located from about 3 mm to about 7 mm from a center of the contact lens.

9. The ocular device of claim 8, wherein the diameter is from about 1 mm to about 2 mm.

10. The ocular device of claim 8, wherein the channel is located from about 4 mm to about 5 mm from the center of the contact lens.

11. The ocular device of claim 8, wherein the channel is substantially cylindrical between the posterior surface and the anterior surface.

12. The ocular device of claim 8, wherein a cross-section of the channel varies between the posterior surface and the anterior surface.

13. The ocular device of claim 8, further comprising an additional channel that is offset from the channel.

14. A kit comprising:
at least one pair of a contact lens having at least one channel, wherein the channel extends between a posterior surface and an anterior surface of the contact lens, wherein the channel has a diameter from about 0.1 mm to about 4 mm, and wherein the channel is located from about 3 mm to about 7 mm from a center of the contact lens; and
an ocular device comprising a hollow tubing extending through a cup member to create an annular space within which a negative relative pressure can be produced and temporarily maintained while the ocular device is in contact with the anterior surface;
wherein the ocular device comprises an elongate element having an outer diameter, which is smaller than an inner diameter of the hollow tubing, wherein the elongate element is axially slideable and removeable with respect to the hollow tubing, and wherein an end of the elongate element is configured to engage with the channel; and
wherein the elongate element comprises a stop near the end configured to prevent the elongate element from penetrating completely through the channel toward a surface of a patient's cornea.

* * * * *